(12) United States Patent
Vasan

(10) Patent No.: US 10,166,386 B2
(45) Date of Patent: Jan. 1, 2019

(54) IMPLANTABLE ELECTRODE ASSEMBLY

(71) Applicant: The Board of Regents of the University of Oklahoma, Norman, OK (US)

(72) Inventor: Nilesh Raman Vasan, Nichols Hills, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 1089 days.

(21) Appl. No.: 14/513,989

(22) Filed: Oct. 14, 2014

(65) Prior Publication Data
US 2015/0105686 A1 Apr. 16, 2015

Related U.S. Application Data

(60) Provisional application No. 61/890,532, filed on Oct. 14, 2013.

(51) Int. Cl.
*A61N 1/05* (2006.01)
*A61N 1/36* (2006.01)
(Continued)

(52) U.S. Cl.
CPC .......... *A61N 1/0556* (2013.01); *A61N 1/0558* (2013.01); *A61B 5/04001* (2013.01);
(Continued)

(58) Field of Classification Search
CPC .............. A61N 1/0558; A61N 1/36082; A61N 1/36064; A61N 1/46053; A61N 1/36003;
(Continued)

(56) References Cited

U.S. PATENT DOCUMENTS

| 4,920,979 | A | * | 5/1990 | Bullara | ................ | A61N 1/0556 |
| | | | | | | 607/118 |
| 5,095,905 | A | * | 3/1992 | Klepinski | ............ | A61N 1/0556 |
| | | | | | | 600/377 |

(Continued)

FOREIGN PATENT DOCUMENTS

WO 2009046764 A1 4/2009

OTHER PUBLICATIONS

Naples, G.G.; "A Spiral Nerve Cuff Electrode for Peripheral Nerve Stimulation"; IEEE Transactions on Biomedical Engineering; vol. 35, No. 11; Nov. 1988; pp. 905-916.

*Primary Examiner* — Eunhwa Kim
(74) *Attorney, Agent, or Firm* — Hall Estill Law Firm

(57) ABSTRACT

An electrode assembly includes a retainer, a flexible sheath, and an electrode. The retainer may include a plurality of clasping arms. The retainer is movable to an open position and a closed position. The flexible sheath is positioned below a lower surface of the retainer. The flexible sheath is at least partially surrounded by the clasping arms of the retainer. The retainer is able to hold the flexible sheath around a target tissue when the retainer is in the closed position. The electrode is configured for conducting electrical signals to or from the target tissue. The electrode is connected to at least one of the retainer and the flexible sheath. The retainer is able to hold the electrode in electrical communication with the target tissue when the retainer is disposed around the target tissue in the closed position.

11 Claims, 11 Drawing Sheets

(51) Int. Cl.
*A61B 5/00* (2006.01)
*A61B 5/04* (2006.01)

(52) U.S. Cl.
CPC ..... *A61B 5/6877* (2013.01); *A61B 2562/0209* (2013.01); *A61N 1/36003* (2013.01); *A61N 1/36053* (2013.01); *A61N 1/36064* (2013.01); *A61N 1/36082* (2013.01)

(58) Field of Classification Search
CPC . A61B 2562/0209; A61B 5/04; A61B 5/6877; A61B 5/0031
USPC .......................................................... 607/118
See application file for complete search history.

(56) References Cited

U.S. PATENT DOCUMENTS

| | | | |
|---|---|---|---|
| 5,215,089 A * | 6/1993 | Baker, Jr. ............ | A61N 1/0556 600/377 |
| 5,531,778 A | 7/1996 | Maschino et al. | |
| 6,600,956 B2 | 7/2003 | Maschino et al. | |
| 7,561,922 B2 | 7/2009 | Cohen et al. | |
| 7,657,310 B2 | 2/2010 | Buras | |
| 8,005,526 B2 | 8/2011 | Martin et al. | |
| 8,417,344 B2 | 4/2013 | Colborn et al. | |
| 8,437,853 B2 | 5/2013 | Inman et al. | |
| 8,457,747 B2 | 6/2013 | Terry, Jr. | |
| 8,478,428 B2 | 7/2013 | Cowley | |
| 8,483,846 B2 | 7/2013 | Maschino et al. | |
| 8,778,420 B1 | 7/2014 | Boyt | |
| 2003/0040785 A1 * | 2/2003 | Maschino ............ | A61N 1/0556 607/118 |
| 2004/0010303 A1 * | 1/2004 | Bolea ................. | A61B 5/02028 607/118 |
| 2006/0136024 A1 | 6/2006 | Cohen et al. | |
| 2009/0210042 A1 * | 8/2009 | Kowalczewski .. | A61B 5/04001 607/118 |
| 2010/0210923 A1 * | 8/2010 | Li .......................... | A61B 5/042 600/301 |
| 2010/0222844 A1 | 9/2010 | Troosters et al. | |
| 2012/0277819 A1 * | 11/2012 | Cowley ................ | A61N 1/0556 607/45 |
| 2013/0253624 A1 * | 9/2013 | Tockman ............ | A61N 1/0558 607/116 |

* cited by examiner

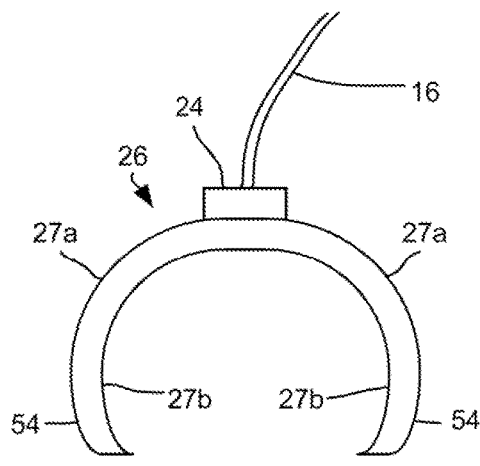 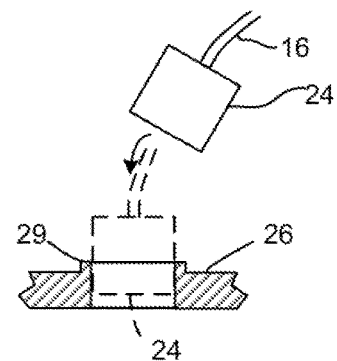
FIG. 2C  FIG. 2D
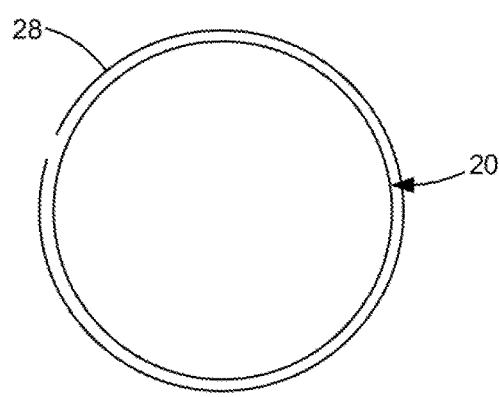 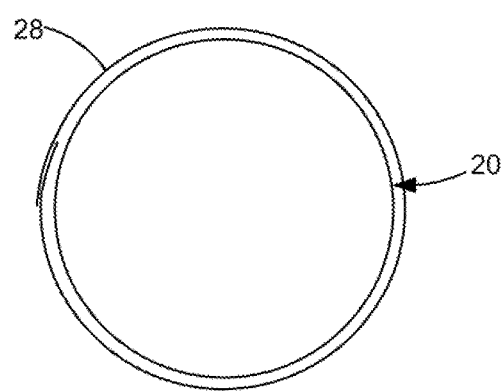
FIG. 2E  FIG. 2F

IMPLANTABLE ELECTRODE ASSEMBLY

RELATED APPLICATIONS

This application claims priority to U.S. Provisional Pat. App. No. 61/890,532 filed on Oct. 14, 2013, entitled "IMPLANTABLE ELECTRODE. ASSEMBLY," the contents of which are incorporated herein by reference.

BACKGROUND

Implantable electrodes can be used stimulate and record from different types of target tissue, including, but not limited to, motor, sensory and mixed peripheral nerves, such as the vagus nerves and renal nerves, and muscle. For example, a traditional nerve cuff electrode assembly is constructed of an electrode, a lead wire from the electrode, and a "cuff" that may hold the electrode in a position against a nerve. The lead wire is attached to an implantable medical device (IMD), such as a power source, which can provide an electric pulse to stimulate the nerve via the electrode.

When the implantable electrode is attached to the target tissue, the IMD can be used to treat and/or help study various medical conditions, e.g., epileptic seizures and depression which can be treated when the implantable electrode is attached to the vagus nerve. However, due to the shape of the traditional cuff, it can be challenging to apply the cuff to the nerve without injury.

Another problem with many of the traditional implantable electrodes currently used is that the portion of the target tissue adjacent the electrode assembly can become infected. When the infection happens, the electrode assembly must be removed. Due to fibrosis upon the cuff over time, it is difficult to remove the cuff and electrode, and the target tissue can be damaged, e.g., potentially causing permanent vocal cord paralysis from vagus nerve injury.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the present disclosure. Further, in the appended drawings, like or identical reference numerals may be used to identify common or similar elements and not all such elements may be so numbered. The figures are not necessarily to scale and certain features and certain views of the figures may be shown exaggerated in scale or in schematic in the interest of clarity and conciseness.

FIG. 2C illustrates a front elevational view of an electrode assembly in accordance with various embodiments.

FIG. 2D provides a partial cross-section of an electrode assembly with a coupling device in accordance with various embodiments.

FIGS. 2E-F demonstrate in schematic a flexible sheath around a target tissue in accordance with various embodiments.

DETAILED DESCRIPTION

Figure 1:
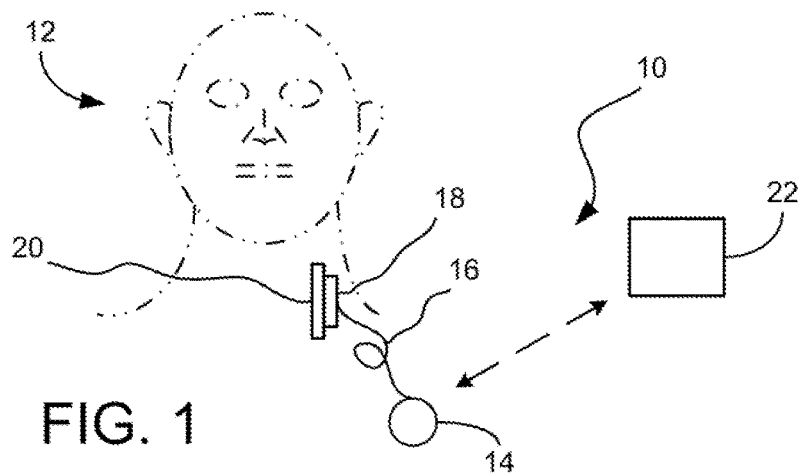
FIG. 1 is as a schematic representation of an implantable device system in accordance with various embodiments that shows a human subject having a subcutaneous vagus nerve stimulation system, having a lead wire extending from a battery-powered pulse generator device to electrodes attached at the left vagus nerve, by way of example.

Before explaining at least one embodiment of the presently described inventive concepts in detail by way of exemplary drawings, experimentation, results, and laboratory procedures, it is to be understood that the inventive concepts are not limited in its application to the details of construction and the arrangement of the components set forth in the following description or illustrated in the drawings, experimentation and/or results. The inventive concepts are capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concepts shall have the meanings that are commonly understood by those of ordinary skill in the art. Further, unless otherwise required by context, singular terms shall include pluralities and plural terms shall include the singular. Generally, nomenclatures utilized herein are those well-known and commonly used in the art. The nomenclatures utilized herein are those well-known and commonly used in the art.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

All of the devices, apparatus, compositions, and/or methods disclosed herein can be made and executed without undue experimentation in light of the present disclosure. While the compositions and methods of this disclosure have been described in terms of particular embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the inventive concepts as disclosed herein.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one, as well as any quantity more than one, including, but not limited to 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results, in addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study items.

As used in this specification and claim(s), the words "comprising" (and any form of comprising, such as "comprise" and "comprises"), "having" (and any form of having, such as "have" and "has"), "including" and any form of including, such as "includes" and "include") or "containing" (and any form of containing, such as "contains" and "contain") are inclusive or open ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, NIB, BBC, AAABCCCC, CBBAAA, CABABB, and so forth. The skilled artisan will understand that typically there is no limit on the number of items or terms in any combination, unless otherwise apparent from the context.

While the presently disclosed inventive concepts will now be described in connection with particular embodiments in the following examples so that aspects thereof may be more fully understood and appreciated, it is not intended to limit the presently disclosed inventive concepts to these particular embodiments. On the contrary, it is intended to cover all alternatives, modifications and equivalents as may be included within the scope of the presently disclosed inventive concepts as described herein. Thus, the following description serves to illustrate the practice of this presently disclosed inventive concepts, it being understood that the particular embodiments shown and discussed are by way of example and for purposes of illustrative discussion of the presently disclosed inventive concepts only and are presented in the cause of providing what is believed to be the most useful and readily understood description of formulation procedures and methods as well as of the principles and conceptual aspects of the presently disclosed inventive concepts.

As used herein, the term "implantable" means capable of being completely or partially implanted, inserted, embedded, and/or grafted into a human or animal body or a natural orifice thereof. A completely implantable device refers to a device having no portions of the device extending outside the body after implantation. A partially implantable device refers to a device which has a portion thereof, such as a lead wire, which extends out of the human or animal body, for example for experimental purposes or for temporary installation periods of time.

As used herein, the terms "implantable device" and "implantable medical device" or "IMD" mean any type of electrical device that is implantable into at human or animal body, and is configured to monitor or affect a function of the body. Examples of implantable medical devices include cardiac pacemakers, nerve stimulation devices, and implantable drug delivery devices.

The term "electrode" or "electrodes" described herein may refer to one or more stimulation electrodes, one or more sensing electrodes, and/or to one or more electrodes that are capable of delivering a stimulation signal as well as performing a sensing function. Stimulation electrodes may refer to an electrode that is capable of delivering a stimulation signal to a tissue of a patient's body. A sensing electrode may refer to an electrode that is capable of sensing a physiological indication of a patient's body. "Electrode" and/or "electrodes" may also refer to one or more electrodes capable of delivering a stimulation signal as well as sensing a physiological indication. An electrode is a conductor that is used to establish electrical contact in a circuit to a nonmetallic part, such as a target tissue.

This disclosure describes an apparatus and method that avoids the previous problems associated with placement and removal of the implantable electrode from the target tissue. Stimulation and sensing of target tissues, such as nerves, have been proposed to treat and diagnose a number of medical conditions. See U.S. Pat. Pub. Nos. 2012/0277819 and 2010/0222844; and U.S. Pat. Nos. 8,483,846, 8,478, 428, 8,778,420, 8,457,747, 8,437,853, 8,417,344, 8,005,526, 7,657,310, 7,561,922, 6,600,956, and 5,531,778; and article *A Spiral Nerve Cuff Electrode for Peripheral Nerve Stimulation*, IEEE Transactions on Biomedical Engineering, volume 35, number 11, November 1998, page 905-916.

FIG. 1 shows a schematic diagram of an exemplary embodiment of an implantable medical device system, indicated generally at 10, implanted in a body 12 of a patient. The implantable medical device system 10 includes an implantable medical device (IMD) 14, a lead wire 16 connected at its proximal end to the IMD 14 and one or more electrode assemblies 18 connected to the lead wire 16 at its distal end. The one or more electrode assemblies 18 may be known as a "lead". A target tissue 20, such as but not limited to nerve or muscle, is connected by the one or more electrode assemblies 18 to the IMD 14 through the lead wire 16, also sometimes known as an electric lead or wire.

The lead wire 16 is a flexible, insulated, electrically conductive wire, and the lead wire 16 may be made from stainless steel or other suitable biocompatible electrical conductor such as, but not limited to titanium wire and platinum-coated stainless steel. The lead wire 16 can include appropriate biocompatible insulation, including, but not limited to, silicone rubber. The lead wire 16 may be braided, multi-strand wires, and the lead wire 16 may include a plurality of wires with one or more wire electrically coupled to each electrode in the one or more electrode assemblies 18.

The IMD 14 typically includes within its housing a microprocessor with digital memory, and a battery (e.g., a rechargeable battery) for providing electrical power to the IMD 14. The IMD 14 can also include a wireless transmitter and an antenna for transmission of signals to an external device, which is outside the body 12, and a GPS transceiver, if desired, for obtaining locational information. The transmitter and antenna can be configured to send and/or receive data and programming and control instructions from an external communications device 22, such as a computer, tablet, smart phone, wristwatch-type device, or other suitable external communications device, with the IMD 14. The transmission and reception is achieved using Bluetooth or some other wireless transmission protocol, allowing the external communications device 22 to receive and transmit data, and perform power-intensive computational operations, so as to conserve power of the IMD 14. If the IMD 14 is partially implanted, then wired transmission protocols can be used to allow the external communications device 22 to receive and transmit data, and perform power intensive computational operations. The external communications device 22 can also be in communication with other external systems, such as a wireless network, wired network, cellular communications system or GPS satellite system, for example. The IMD 14 may have use in a variety of settings, e.g., therapeutics, diagnostics, or both therapeutics and diagnostics.

FIGS. 2A-F illustrate the electrode assembly 18 in accordance with some embodiments. The electrode assembly 18 is configured for conducting electrical signals between the IMD 14 (see FIG. 1) and the target tissue 20. The electrode assembly 18 may comprise one or more electrodes 24 that are electrically connected, or in electrical communication, to the lead wire 16. A retainer 26 is connected to the electrode 24 in some embodiments. In some embodiments, the electrode 24 is detachably connected to the retainer 26. In one embodiment, the retainer 26 is electrically connected to the electrode 24. In another embodiment, the retainer 26 is not electrically connected to the electrode 24. The retainer 26 is configured to facilitate retention of the electrode 24 in electrical communication with the target tissue 20. In one embodiment, the electrode 24 is in contacting engagement with the target tissue 20. In another embodiment, the electrode 24 is adjacent the target tissue 20 and less than about 0.5 mm from the target tissue 20. Other distances between the electrode 24 and the target tissue 20 are possible, for example, the electrode 24 is adjacent the target tissue 20 and separated from the target tissue 20 by a distance of at least about 0.5 mm or at least about 1.0 mm.

A flexible sheath 28 is connected to the retainer 26. The flexible sheath 28 is not electrically connected to the electrode 24 or the retainer 26. In one embodiment, the flexible sheath 28 is detachably connected to the retainer 26. In some embodiments, the electrode 24 is detachably connected to the flexible sheath 28. In certain embodiments, the electrode 24 is connected to at least one of the retainer 26 and the flexible sheath 28. In the embodiment illustrated in FIGS. 2A-D, the retainer 26 comprises a plurality of clasping arms 54 which extend from a stem 30. Each arm 54 has an upper surface 27*a* and a lower surface 27*b*.

The electrode 24 can be configured to be removed from the body 12 (see FIG. 1) by a simple operation, a procedure with minor manipulation of the electrode assembly 18 using instruments without violation of the retainer 26 and therefore the risk of injury to the target tissue 20 is minimized or eliminated. In addition, the connection between the electrode 24 and the retainer 26 can be configured to be potentially reversible, i.e., the electrode 24 can be detachably connected to the retainer 26 such that the electrode 24 and the retainer 26 can be decoupled, and the electrode 24 or a substitute electrode 24 can be reattached to the retainer 26 via a coupling device 29 within the retainer 26. The coupling device 29 may comprise, but is not limited to, a connection such as "pin-socket", "male-female", "plug-socket" or other such coupling devices known by persons having ordinary skill in the art. In one embodiment, the retainer 26 could also be removed from the flexible sheath 28 with or without the electrode 24 also being removed from the body 12. In one embodiment for example the retainer 26 has severable connectors such as "studs" between the retainer 26 and the flexible sheath 28 that could allow separation, or severing, of the retainer 26 from the flexible sheath 28 by simple division of the studs, which could be made of any suitable biocompatible, including, but not limited to, silicone elastomer material (see the discussion of FIG. 6 for further details of this embodiment).

The lead wire 16 may be configured to be in substantially parallel alignment with the electrode assembly 18 and the electrode 24, such that the lead wire 16 may lie substantially parallel to the target tissue 20, e.g., parallel to a longitudinal axis of a nerve. However, the lead wire 16 could be configured to be in a different orientation to the electrode assembly 18 and the electrode 24, such that the lead wire 16 may lie other than substantially parallel to the target tissue 20, e.g., not parallel to a longitudinal axis of a nerve. For example, the lead wire 16 could be configured to be substantially orthogonal to the electrode assembly 18 and the electrode 24, but such orientation is merely exemplary and not limiting. The orientation of the lead wire 16 can be configured based on need of the IMD 14, and such needs may include the anatomy of the body 12. When implanted in the body, the electrode 24, the retainer 26, or the flexible sheath 28 may support the lead wire 16 to reduce help tension or traction on the lead wire 16, which may help prolong the useful life of the lead wire 16 after implantation.

For simplicity, one electrode 24 is shown; however, in other embodiments multiple electrodes (e.g., 2, 3, 4, 5, or more) can be used, as disclosed herein elsewhere. The electrode 24 can be used for stimulating, sensing, or both sensing and stimulating. The electrode 24 is configured for conducting electrical signals between the IMD 14 and the target tissue 20.

The flexible sheath 28 is configured to be contactingly adjacent the target tissue 20 when the electrode assembly 18 is placed in the body 12. In another embodiment, the flexible sheath 28 is configured to be adjacent the target tissue 20 and less than 0.5 mm from the target tissue 20 when the electrode assembly 18 is placed in the body 12. The flexible sheath 28 may be electrically insulative when the electrical flexible sheath 28 includes high impedance material. The electrical insulation is provided such that the electrode 24 is able to stimulate or sense the target tissue 20 while minimizing extraneous stimulation of or recording from the surrounding tissue, respectively. There are a variety of biocompatible insulative materials that can be used. The flexible sheath 28 can be made of silicone, such as silicone elastomer MED-4750 manufactured by NuSil. Other insulative materials, such as polytetrafluoroethylene (PTFE), polyethersulfone, collagen, poly-amino acids, silks, elastins, polyester, polyether, poly-4-hydroxybutyrate (P4HB), or other similar materials can also be used.

The flexible sheath 28 may be electrically conductive when the flexible sheath includes biocompatible low impedance material. In some embodiments, the flexible sheath 28 can be made of conducting polymers that can include, but are not limited to poly(3,4-ethylenedioxythiophene) (PEDOT), poly(pyrrole), polyanilines, polyacetylenes, poly(diallyldimethylammonium chloride), poly-4-vinylpyridine, poly(vinylalcohol), polythiophenes, polymer blends thereof, and composites with the ability to conduct electronic charge or ions, and hybrid polymer materials that are electrically or ionically conductive. Other electrically conductive materials may include, but are not limited to, polymers, such as polyfluorene, polyphenylenes, polypyrenes, polyazulenes, polynaphthalenes, polycarbazole, polyindole, polyazepine, poly(thiophene) (PT), poly(p-phonylene sulfide) (PPS), and poly(p-phenylene vinylene) (PPV).

Figure 2A:
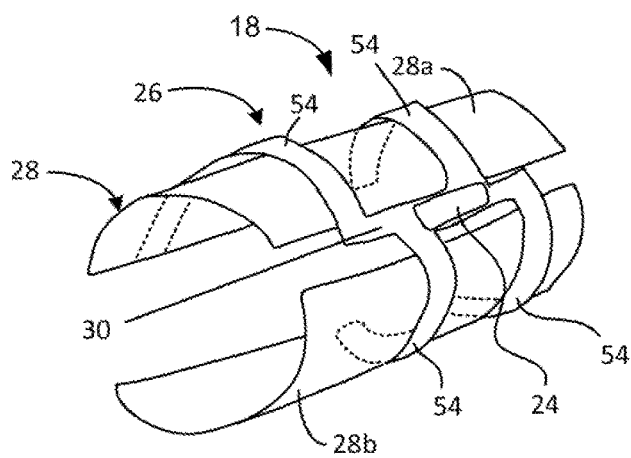
FIGS. 2A-B shows perspective views of an electrode assembly in accordance with various embodiments.
Figure 2B:
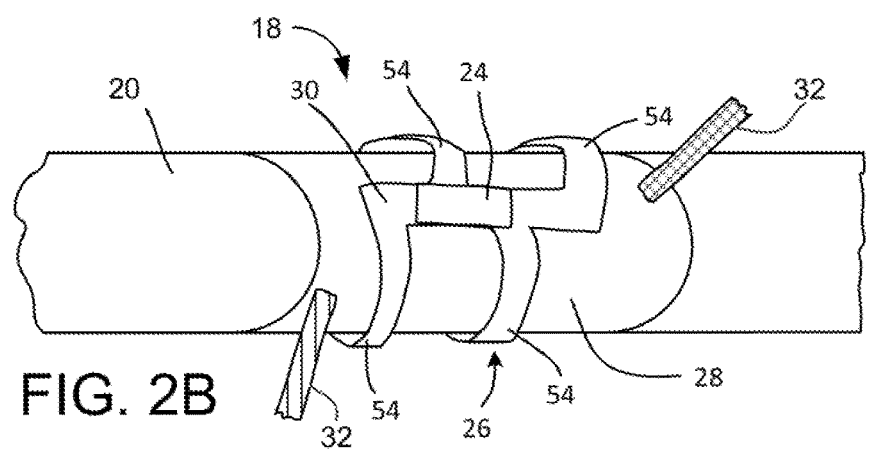

The shape, size and configuration of the flexible sheath 28 can vary. The flexible sheath 28 is sized or shaped to be adjacent the target tissue 20 without overlap of the flexible sheath 28 on itself in some embodiments, while the flexible sheath 28 is sized or shaped to be adjacent the target tissue 20 with overlap of the flexible sheath 28 on itself in other embodiments. The flexible sheath 28 may include 2 or more physically separate sheets 28a and 28b as shown in FIG. 2A, or the flexible sheath 28 may include a single sheet as shown in FIG. 2B. In addition, the flexible sheath 28 may include both high impedance material and low impedance material that are sized and positioned in the flexible sheath 28 to achieve electrical insulation and electrical conduction as needed.

The retainer 26 might be considered a reinforcing member for the flexible sheath 28. The retainer 26 may be composed of substantially the same or substantially different biocompatible materials as the flexible sheath 28. The retainer 26 may be substantially thicker, substantially thinner, or substantially the same thickness as the flexible sheath 28. As with the electrode assembly 18, the retainer 26 may be composed of silicone rubber, or another biocompatible, durable polymer such as siloxime polymers, polydimethylsiloxanes, polyurethane, polyether urethane, polyetherurethane urea, polyestentrethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. In addition, the electrode assembly 18, including the electrode 24 and/or the retainer 26, may be composed of a pure metal, or a metal alloy, such as, but not limited to, approximately 80% platinum/approximately 20% iridium, approximately 90% platinum and the remainder iridium, iridium oxide, or other precious metals or their alloys or oxides. The metal or metal alloy may comprise any biologically-compatible electrically conductive metal or metal alloy. Further, in some embodiments, the retainer 26 can be made of biocompatible graphene, which has high electrical conductivity. In addition to providing for electrical conduction, the material in the retainer 26 may provide structural strength to the retainer 26 and facilitate retention of a shape memory by the retainer 26.

The retainer 26 is configured to facilitate retention of the flexible sheath 28 between the target tissue and the retainer 26. In one embodiment, the flexible sheath 28 is biased toward a substantially cylindrically wrapped configuration. That is, the flexible sheath 28 can be formed to naturally rest in the substantially cylindrical shape shown in FIGS. 2A-B. This shape facilitates implantation of the electrode assembly 18 because the shape requires less effort on the part of an implanting surgeon to bend the overwrap into the cylindrical shape, since the flexible sheath 28 naturally has a memory of a substantially cylindrical shape already built in. Methods for producing silicone material with a memory or pre-biased shape, such as by injection molding and extrusion are well known to those of skill in the art.

Prior to the attachment of the electrode assembly 18 to the target tissue 20, the lead electrode assembly 18 is expanded by the surgeon and aligned on the target tissue 20. When the electrode assembly 18 is properly positioned on the target tissue 20, the surgeon releases the retainer 26, which will naturally revert to its preformed substantially cylindrical shape, and encase or clamp onto the target tissue 20 with the flexible sheath 28 positioned between the target tissue 20 and the retainer 26. The shape memory of the material and the design characteristics of the retainer 26, cause the retainer 26 to return to its closed position, which in turn secures the electrode assembly 18 to the target tissue 20. The pressure of the retainer 26 in the closed position is adequate to gently hold the electrode assembly 18 in place on the target tissue 20.

The electrode 24 needs to be in electrical communication with the target tissue 20 in order to stimulate or sense the target tissue 20. The electrode 24 may be held, in a substantially fixed relationship with the target tissue 20 to improve stimulation and sensing of the target tissue 20. Retention of the substantially fixed relationship between the electrode 24 and the target tissue 20 is facilitated by the retainer 26.

Further, minimizing stimulation of and sensing from the surrounding, tissue adjacent the target tissue 20 may be useful. Minimizing stimulation of the surrounding tissue will decrease the amount of energy that needs to be provided by the IMD 14 (see FIG. 1) to achieve a certain stimulation goal in the target tissue 20. Reducing the amount of energy needed by the IMD 14 to achieve stimulation goals will prolong the battery life of the IMD 14, which means the IMD and the IMD 14 battery may need to be replaced, or recharged less frequently. Further, minimizing stimulation of the surrounding tissue may reduce discomfort or other side effects from the stimulation that is experienced by the patient. The stimulation threshold to achieve a desired result in the target tissue 20 may be less, also.

Minimizing sensing from the surrounding tissue will decrease the amount of energy that needs to be provided by the IMD 14 (see FIG. 1) to achieve a certain sensory acquisition data from the target tissue 20. The signal to noise ratio in the sensed signal may be reduced in recording from the target tissue 20, also. Such examples of the benefits of minimizing stimulation of and sensing from the surrounding tissue are exemplary and not limiting.

Minimizing stimulation of and sensing from the surrounding, tissue, while maximizing stimulation of and sensing from the target tissue 20 may be achieved, by using a sheath. In certain prior conventional versions of electrode assemblies, a nerve cuff electrode has included an electrode, a retainer, and a sheath. In the traditional arrangement of the electrode, the retainer, and the sheath in the nerve cuff electrode, an electrode is in electrical communication with the nerve, i.e., the target tissue 20, a retainer is attached to the electrode to facilitate retention of the electrode in electrical communication with the target tissue, and a sheath covers or is wrapped externally over both the electrode and the retainer to provide a high impedance, otherwise known as a high resistance barrier between the electrode and the surrounding (non-target) tissue and possibly other electrodes in the electrode system. In addition, the sheath in this arrangement may help fixate the electrode in relation to the target tissue 20. Unfortunately, if the electrode, the retainer, or both the electrode and retainer need to be removed from the body, then the electrode, the retainer, and the sheath overlying the electrode and the retainer must be removed. The sheath overlying the electrode and the retainer must be removed in order to gain access to the electrode and the retainer.

Moreover, when an electrode assembly such as a conventionally available electrode assembly is surgically implanted in a body, the target tissue 20 may be damaged during the process of exposing the target tissue 20 for placement of the electrode assembly. Further, the target tissue 20 may be damaged during and after placement of the electrode assembly adjacent the target tissue 20. After the electrode assembly is surgically implanted in the body 12, scarring and fibrosis may occur in and around electrode assembly, which may lead to further damage of the target tissue 20 and may affect operational ability of the electrode assembly. In certain cases it may be desirable or necessary to remove the electrode of the electrode assembly. However, as previously noted, scarring and fibrosis may make removal of all or part of the electrode assembly difficult or impossible to perform without temporary or permanent damage to the target tissue.

When the target tissue 20 is a nerve, neurapraxia is an injury that interrupts neural conduction causing temporary loss of function but not degeneration, and it may be followed by complete and rapid recovery. When the target tissue 20 is a nerve, axonotmesis is an injury that damages the axon but does not completely sever the surrounding endoneurial sheath such that regeneration may occur. When the target tissue 20 is a nerve, neurotmesis is an injury that disrupts both the axon and the endoneurial sheath such that complete recovery is impossible.

Of course, nerve is a nervous tissue. However, the target tissue 20 can be non-nervous tissue. An exemplary non-nervous tissue is muscle tissue. Other target tissues are contemplated, such as solid organs.

While the electrode assembly may be placed to treat and diagnose a variety of medical conditions, it may become necessary to remove the electrode assembly or components thereof for various reasons, including infection. Although it may be beneficial to remove the entirety of the electrode assembly, removal of portions of the electrode assembly that contain metal may be most important, particularly in the case of infection in and around the electrode assembly. However, with conventional systems, it is difficult to remove the entire electrode assembly or even individual portions thereof. In embodiments of the presently disclosed inventive concepts it is possible to remove the electrode 24 or both the electrode 24 and the retainer 26, while leaving the flexible sheath 28 in the body, thereby avoiding damage to the target tissue 20.

Returning now to the drawings, as shown in FIGS. 2A-B, the flexible sheath 28 is positioned below the lower surfaces 27b of the clasping arms 54 of the retainer 26 such that the flexible sheath 28 is positioned substantially between the target tissue 20 and the retainer 26. The flexible sheath 28 is at least partially surrounded by the clasping arms 54 of the retainer 26. In other words, the disclosed arrangement places the retainer 26 further from the target tissue 20, with the flexible sheath also known as under-sheath) 28 between the retainer 26 and the target tissue 20. The flexible sheath 28 may facilitate distribution of pressure over the target tissue 20 to reduce intensity of pressure points on the target tissue 20 produced by the retainer 26.

Furthermore, in this embodiment it becomes possible to remove the electrode 24, or the retainer 26, or both the electrode 24 and the retainer 26 from the body 12 without having to remove the flexible sheath 28 from the target tissue 20 of the body 12. The electrode 24 (and optionally the retainer 26) contains metal. When the target tissue 20 at the site of the electrode assembly 24 becomes infected the metal components of the electrode assembly (i.e., the electrode 24 and optionally the retainer 26), need to be removed from the setting of infection, in order for the infection to be successfully treated. On the other hand, the flexible sheath 28 in the present embodiment does not have metal and may be left in the body when the infection is successfully treated. There may be other medical conditions in which removal of the electrode 24, or the retainer 26, or both electrode 24 and the retainer 26 without removal of the flexible sheath 28 may prove useful.

As noted above, in conventionally available prior art systems it is impossible to remove the retainer and electrode without also having to remove or disrupt the flexible sheath. Thus, in the presently disclosed, inventive concepts the electrode 24 is adapted to minimize damage to the target tissue 20 from removal of the electrode 24 from electrical communication with the target tissue 20. Further, the retainer 26 is adapted to minimize damage to the target tissue 20 from removal of the retainer 26. The retainer 26 is adapted for removal of the electrode 24 from electrical communication with the target tissue 20 without substantial disruption or damage to the target tissue 20. The flexible sheath 28 is adapted to remain adjacent the target tissue 20 after removal of the electrode 24 or both the electrode 24 and the retainer 26.

FIGS. 3A-C and 4A-C illustrate exemplary embodiments of the electrode 24 and the retainer 26 and the flexible sheath 28, respectively. The electrode 24 can take any shape depending on need, and in this case is shown as a square. The electrode 24 can be identified by a tag 32 which may be useful during placement or removal of the electrode assembly 18 (see FIGS. 2A-B). The tag 32 can be made of any flexible biocompatible nonabsorbable material, including, but not limited to, PROLENE® polypropylene sutures (clear or pigmented), which are available from Ethicon, a part of the Johnson & Johnson Family of Companies. (Prolene is a registered trademark of Johnson & Johnson Corporation, One Johnson & Johnson Plaza, New Brunswick, N.J., at the time this provisional application is filed.) The PROLENE® polypropylene sutures are composed of an isotactic crystalline steroisomer of polypropylene, a synthetic linear polyolefin, however this flexible biocompatible nonabsorbable material is exemplary and not limiting. In accordance with various embodiments, the tag 32 may be pigmented to enhance visibility.

Figure 3A:
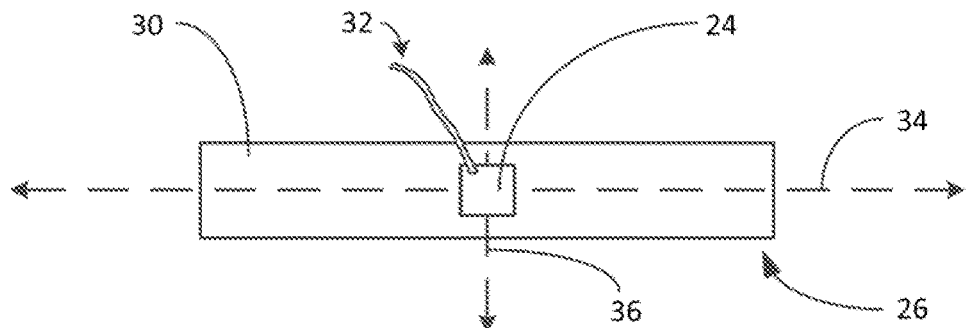
FIGS. 3A-C demonstrates views from the electrode side of the electrode assembly in accordance with various embodiments.
Figure 3B:
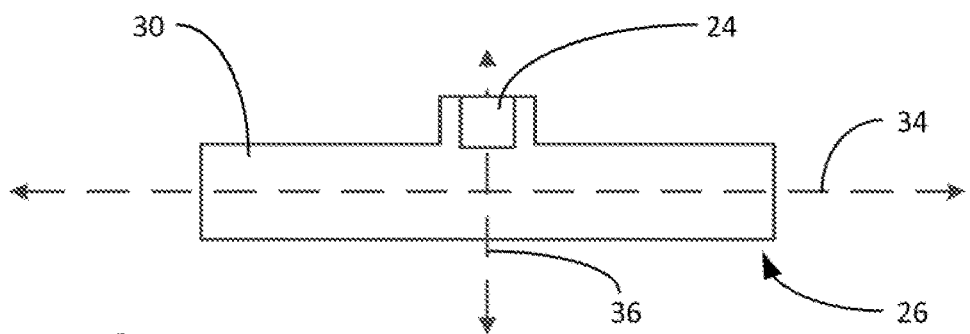
Figure 3C:
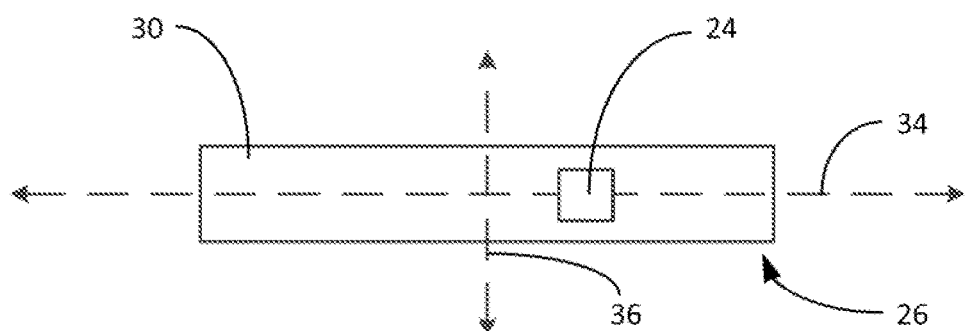

The electrode 24 may be may be connected in a substantially fixed relationship to the retainer 26 in a variety of ways, and the position of the electrode 24 in relation to the retainer 26 can encompass any variation of width, length, or height of either the electrode 24 or the retainer 26 and any orientation of the electrode 24 in relation to the retainer 26. Several exemplary arrangements are shown; however, these arrangements are merely exemplary and not limiting. In one embodiment, the retainer 26 has the stem 30 that is adapted to lie substantially parallel to the long axis of the target tissue (see FIG. 2B), including, but not limited to, the nerve, more specifically the nerve axon, whether efferent or afferent. The stem 30 has an elongated longitudinal axis 34 and a width axis 36 that is shorter and substantially perpendicular to the elongated longitudinal axis 34. FIG. 3A shows the electrode 24 may be substantially fixed in relation to the retainer symmetrically along the elongated longitudinal axis 34 and the width axis 36. FIG. 3B shows an embodiment in which the electrode 24 is asymmetrically placed along the width axis 36. FIG. 3C shows an embodiment in which the electrode 24 is asymmetrically placed along the elongated longitudinal axis 34. Any and all combinations of the electrode 24 in relation to the retainer 26 are contemplated.

The electrode 24 can be any shape or size, including length, width, and depth, and the position of the electrode 24 in relation to the retainer 26 can include any variation of the width, length or height (or depth) for either the electrode 24, the retainer 26 or the electrode 24 and the retainer 26. For example, the dimensions of the electrode 24 may have a width of from about 0.1 mm to about 2.0 mm, and a length of from about 0.1 mm to about 10 mm. Connection pads (not shown) may be provided with dimensions sufficient to allow good electrical connection between the electrode 24 and the lead wire 16, which will vary according the application. In one embodiment, the connection pads may be provided with length and width dimensions ranging from about 20 µm to about 3 mm. In other embodiments, the retainer 26 is sized to wrap around the target tissue 20 by providing an inner diameter from about 2 mm to about 3 mm to accommodate the target tissue, such as the vagus nerve. In some embodiments, the stem 30 has a length of from about 2 mm to about 300 mm (typically about 5 mm), a width of from about 0.5 mm to about 12.0 mm, and depth of about 1 mm to about 5 mm. In other embodiments, the flexible sheath 28 has a thickness of from about 0.1 mm to about 1.27 mm (typically about 0.127 mm, which is 0.005 inches), a length of from about 4 mm to about 400 mm (typically about 5 mm), and a width of from about 6.0 mm to about 15.0 mm.

The relationship of the electrode 24 to the retainer 26 has implications for how the electrode 24, the retainer 26, and the flexible sheath 28 interact. Further, depending on the arrangement of the electrode 24, the retainer 26, and the flexible sheath 28, the electrode 24, the retainer 26, or the flexible sheath may need to provide for a high impedance barrier or a low impedance barrier to support stimulation to or sensing from the target tissue 20.

In one embodiment, the flexible sheath 28 is constructed of a high impedance material forming a high impedance barrier. In this embodiment, the flexible sheath 28 cannot be disposed between the electrode 24 and the target tissue 20, otherwise the electrode 24 will not be in electrical communication with the target tissue 20 (see FIGS. 2A-B).

In another embodiment, the flexible sheath 28 is constructed of a low impedance material forming a low impedance barrier. In the low impedance embodiment, the flexible sheath 28 can be disposed between the electrode 24 and the target tissue 20 so that the electrode 24 is in electrical communication with the target tissue. When the flexible sheath 28 is made of low impedance (also known as electrical conductor) material, then an opening or aperture in the flexible sheath 28 to permit the electrode 24 to be in electrical communication with the target tissue 20 is optional and not required.

The flexible sheath 28 can be made of a combination of one or more high impedance materials and one or more low impedance materials, such that electrical conduction through the flexible sheath 28 can occur in the low impedance areas and electrical conduction through the flexible sheath 28 does not occur in the high impedance areas. However, metal, or more generally material that will cause a problem when left behind in the setting of infection or other medical condition, will be excluded from the flexible sheath 28 so that the flexible sheath 128 may be left in the body 12 when the electrode 24, the retainer 26, or both the electrode 24 and the retainer 26 are removed from the body 12.

FIGS. 2E-F illustrate in schematic the flexible sheath 28 around the target tissue 20. The flexible sheath 28 is adjacent the target tissue 20. In some embodiments, the flexible sheath 28 is in contacting engagement with the target tissue 20. FIG. 2E shows the flexible sheath 28 configured to wrap around the target tissue 20. The flexible sheath 28 is wrapped less than 360° around the target tissue 20. FIG. 2F shows the flexible sheath 28 configured to wrap around the target tissue 20, such that the flexible sheath 28 is substantially wrapped around an entire circumference (i.e., 360°) of the target tissue 20.

Figure 4A:
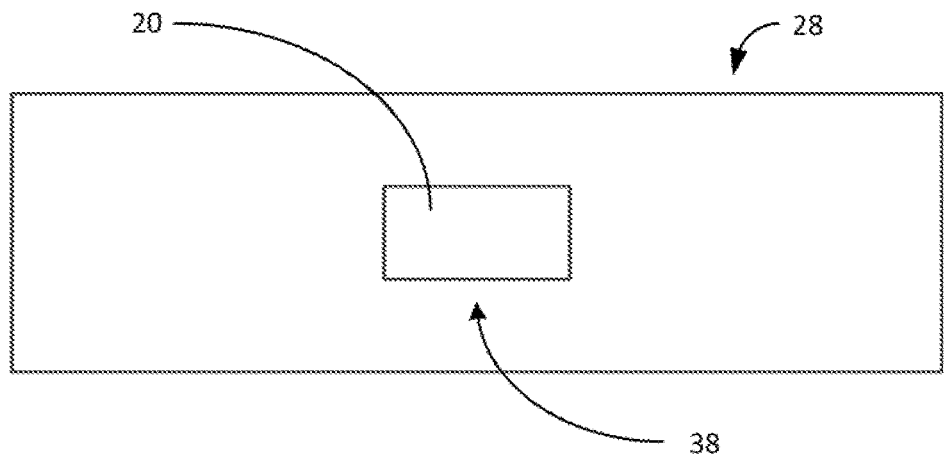
FIGS. 4A-C illustrate top views of a flexible sheath in accordance with various embodiments.

FIG. 4A shows a relatively simple arrangement in which the flexible sheath 28 provides an aperture 38 that allows the electrode 24 to be in electrical communication with the target tissue 20 when placed over or in the aperture 38. The corresponding arrangement of the electrode 24 to the retainer 26 can optionally include those embodiments shown in FIGS. 3A-C and other contemplated arrangements, for example.

Figure 4B:
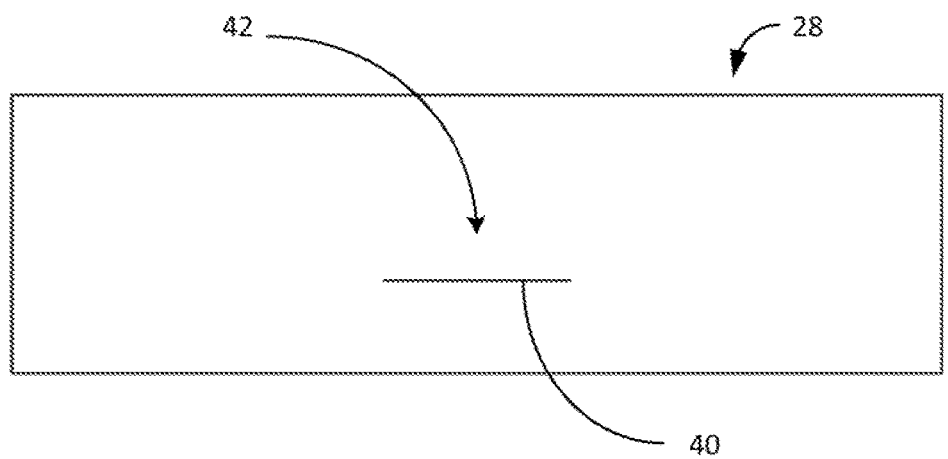
Figure 4C:
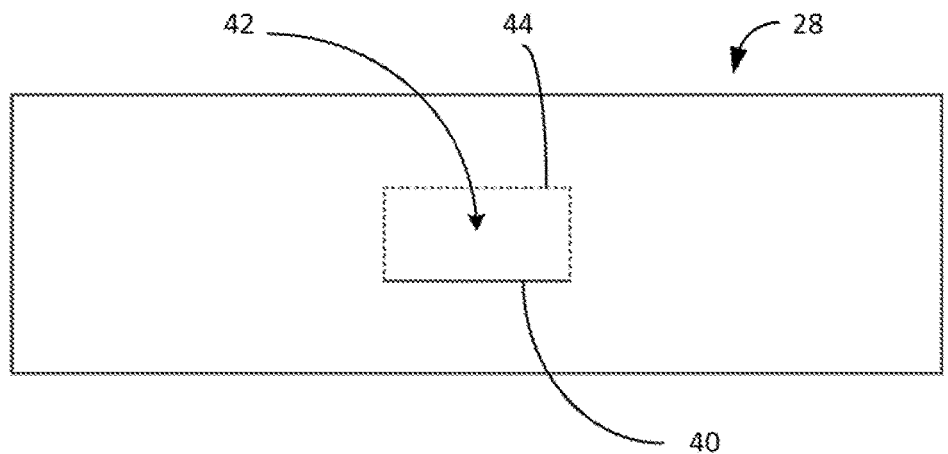

FIGS. 4B-C show the flexible sheath 28 provides a side aperture 40 (e.g., a cut or slit) that allows the electrode 24 to slide under a portion 42 of the flexible sheath 28, such that the electrode 24 can be in electrical communication with the target tissue 20, when the portion 42 of the flexible sheath 28 is made of high impedance material. The arrangement of the electrode 24, the retainer 26 and the flexible sheath 28 in this and all embodiments contemplated can be arranged during manufacture or later. The corresponding arrangement of the electrode 24 to the retainer 26 can optionally include those embodiments shown in FIG. 3B and other contemplated arrangements, for example.

In FIG. 4C, the side aperture 40 is augmented by a tear away feature 44. The tear away feature 44 may comprise perforations or thin areas in the material of the flexible sheath 28, or any other means known in the art for forming weakened portions of material. The tear away feature 44 of the flexible sheath 28 functions such that when the surgeon attempts to remove the electrode 24, the electrode 24 will not only be able to slide out of the side aperture 40 as in FIG. 4B, but the electrode 24 will be able to separated from the flexible sheath 28 by the tear away feature 44 giving way.

Figure 5A:
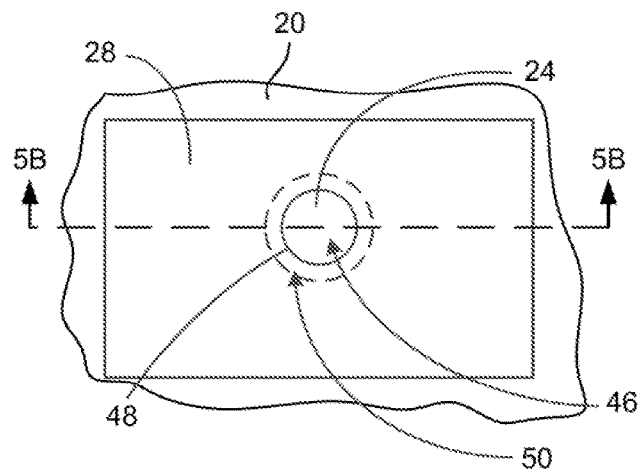
FIG. 5A is a top view of an electrode and a flexible sheath in accordance with various embodiments.
Figure 5B:
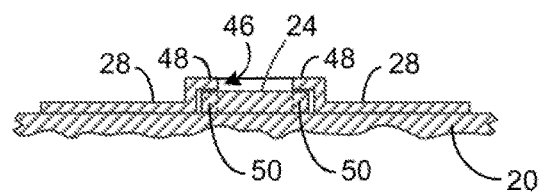
FIG. 5B is a cross-sectional view of FIG. 5A in accordance with various embodiments.
Figure 5C:
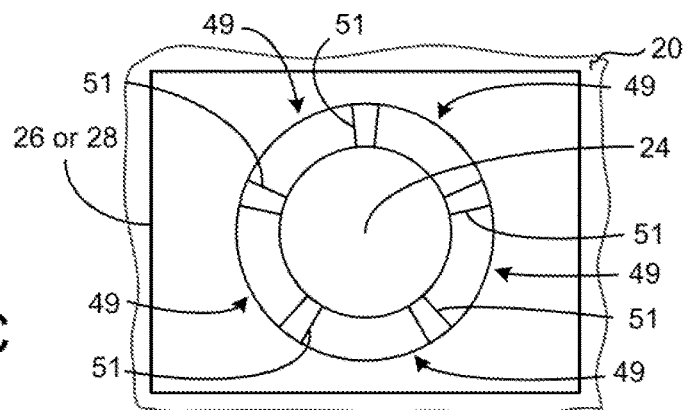
FIG. 5C is a top view of an electrode and a retainer or a flexible sheath in accordance with various embodiments.

Other embodiments of how the electrode 24, the retainer 26, and the flexible sheath 28 are engaged are shown in FIGS. 5A-C. For example, FIG. 5A demonstrates an embodiment showing the flexible sheath 28 may provide an aperture 46 that is configured to facilitate removal of the electrode 24 from electrical communication with the target tissue 20. The electrode 24 is sized or shaped to be disposed between the flexible sheath 28 and the target tissue 20 when the electrode 24 is in electrical communication with the target tissue 20 and the flexible sheath 28 is adjacent the target tissue 20. The aperture 46 of the flexible sheath 28 provides a retention lip 48. The electrode 24 provides a retention edge 50.

FIG. 5B shows a cross-sectional view of 5A that shows the relationship between the flexible sheath 28 that provides the retention lip 48 that engages the retention edge 50 of the electrode 24 to facilitate retention of the electrode 24 in electrical communication with the target tissue 20, and the electrode 24 adjacent the target tissue 20. The flexible sheath 28 is adjacent the target tissue 20, also. The aperture 46 of the flexible sheath 28 is dimensioned or sized to be smaller than the retention edge 50 to retain the electrode 24 in electrical communication with the target tissue. While any shape, size, and orientation of the retention lip 48 and the retention edge 50 can be used, if the retention lip 48 is substantially circular, then it may be easier to size the electrode 24 and the retention edge 50 to facilitate retention of the electrode. It is analogous to why manhole covers in the street are substantially circular rather than another shape.

FIG. 5C illustrates other another embodiment in which the electrode 24 is retained in an aperture 49 by a plurality of connectors 51, which are made of any suitable biocompatible materials, but not limited to, silicone rubber. The aperture 49 is provided by the retainer 26, the flexible sheath 28, or both the retainer 26 and the flexible sheath 28, so that the electrode 24 can be in electrical communication with the target tissue 20. The plurality of connectors 51 hold the electrode 24 in a substantially fixed relationship to the target tissue 20 after placement of the electrode 24 in the body 12 (see FIG. 1). The plurality of connectors 51 can be severed to remove the electrode 24 from either the retainer 26, the flexible sheath 28, or both the retainer 26 and the flexible sheath 28. While five connectors 51 are shown in FIG. 5C, one or more connectors 51 are contemplated to be of any size and shape.

Figure 6:
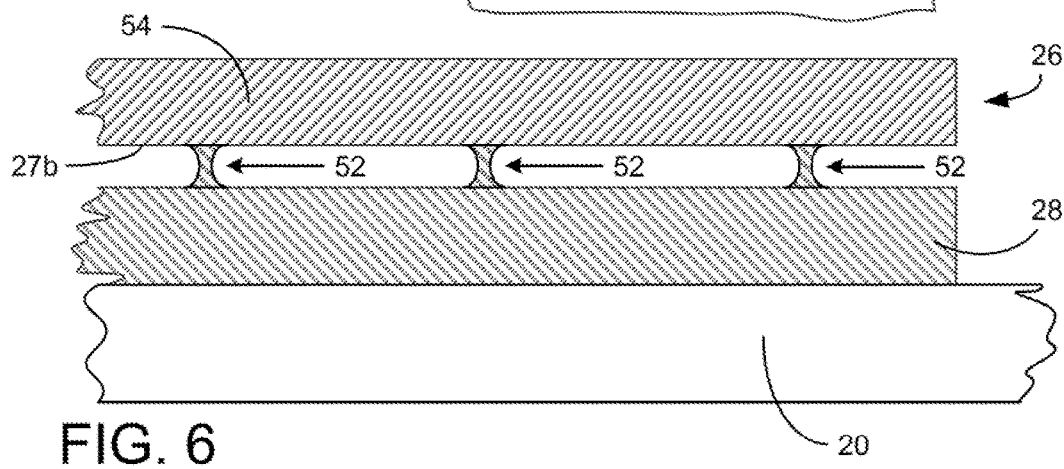
FIG. 6 is a side view of a retainer connected to a flexible sheath adjacent a target tissue in accordance with some embodiments.

FIG. 6 shows an arrangement of the retainer 26 and the flexible sheath 28, in which a plurality of studs (a.k.a. connectors or spacers) 52 serve to connect portions of the flexible sheath 28 to portions of the lower surfaces 27b of the clasping arms 54 of the retainer 26. When it is desired by the surgeon to remove the retainer 26, the plurality of studs 52 are severed thereby decoupling the retainer 26 from the flexible sheath 28. The flexible sheath 28 is adapted to remain adjacent the target tissue 20 when the retainer 26 is decoupled from the flexible sheath 28 and removed from the body 12. The stud 52 may be implemented through any appropriate biocompatible tear away feature such as weakening the connection between the retainer 26 and the flexible sheath 28 through material. Of course, the coupling between the retainer 26 and the flexible sheath 28 would need to be strong enough to survive manipulation by the surgeon during implantation and use of the retainer 26 and the flexible sheath 28 by the user with the IMD 14, for example. FIG. 6 shows an embodiment in which three studs 52 connect the retainer 26 and the flexible sheath 28, although greater than three or fewer than three studs 52 are also contemplated. There may even be effectively one stud 52 that is essentially continuous between the retainer 26 and the flexible sheath 28.

Figure 7A:
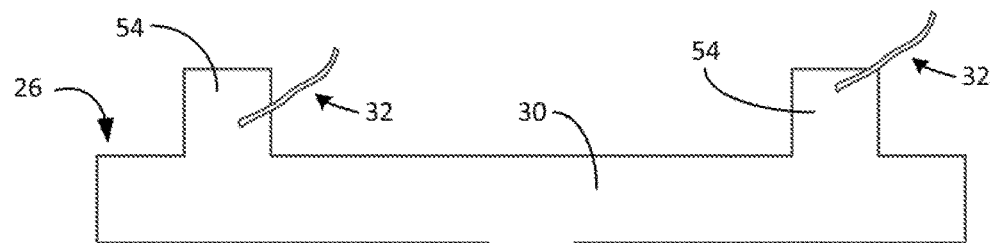
FIGS. 7A-C show top views of a retainer in accordance with various embodiments.
Figure 7B:
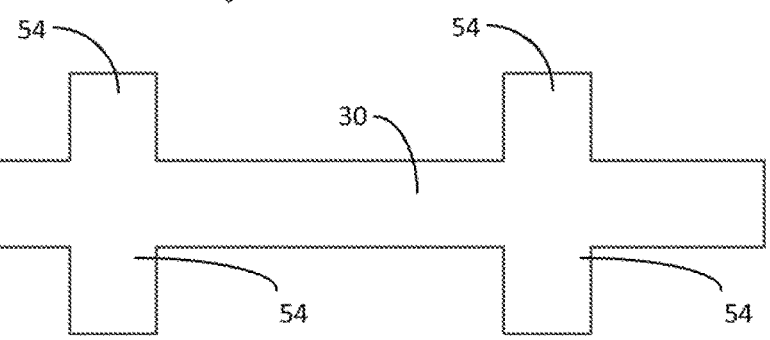
Figure 7C:
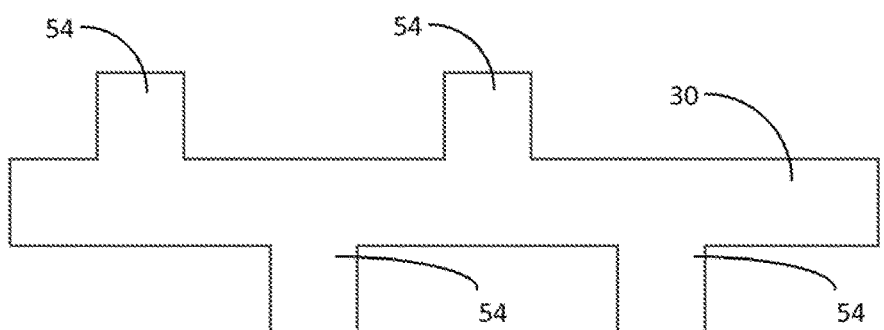

FIGS. 7A-C show in top view and FIG. D shows in bottom view various configurations of alternate embodiments of the retainer 26 having the stem 30 that provides a plurality of clasping arms 54 (or arms) in accordance with various embodiments. The clasping arms 54 are shown substantially orthogonal to the stems 30, however other orientations are possible. As discussed earlier, the retainer 26 may include the stem 30 that provides the elongated longitudinal axis 34 (see FIGS. 3A-C) that is substantially parallel to the target tissue 20, such as a nerve. The stem 30 is adapted to extend lengthwise along the target tissue 20 and to provide a plurality of clasping arms 54 that extend widthwise (i.e., perpendicularly) from the stem 30.

FIG. 7A shows three clasping arms 54 extending from stem 30 arranged asymmetrically about the elongated longitudinal axis 34 (see FIGS. 3A-C) of the retainer 26. The tag (discussed above in relation to FIG. 3A) can be attached to each of the clasping arms 54. The tag 32 may facilitate placement of the retainer 26 around the target tissue 20 or identification of the clasping arms 54 when the surgeon attempts to remove the retainer 26 from the body. For example, the surgeon might manipulate the tag 32 to open or close the clasping arms 54. As another example, the tag 32 may be help make the electrode assembly 18 (see FIGS. 2A-B) more visible in the setting of infection, fibrosis, or scarring. When a surgeon needs to remove the electrode assembly 18 for whatever reason including, but not limited to, infection, the tag 32 resting on tissue other than the target tissue 20, including, but not limited to nerve and muscle, may be more visible. In certain embodiments, the tag 32 can have an indicia, such as but not limited to color coding from pigmentation, that indicates whether the tag 32 is attached to the electrode 24, the retainer 26 or the flexible sheath 28. In accordance with certain embodiments, the tag 32 has an orientation indicia such that the surgeon can place the electrode assembly 18 with a rostral indicia associated with the tag 32 towards the head of the body, a caudal indicia associated with the tag 32 towards the tail (or cauda) of the body, a medial indicia associated with the tag 32 towards the midline of the body, a lateral indicia associated with the tag 32 away from the midline of the body, or any combination of orientation indicia.

Figure 7D:
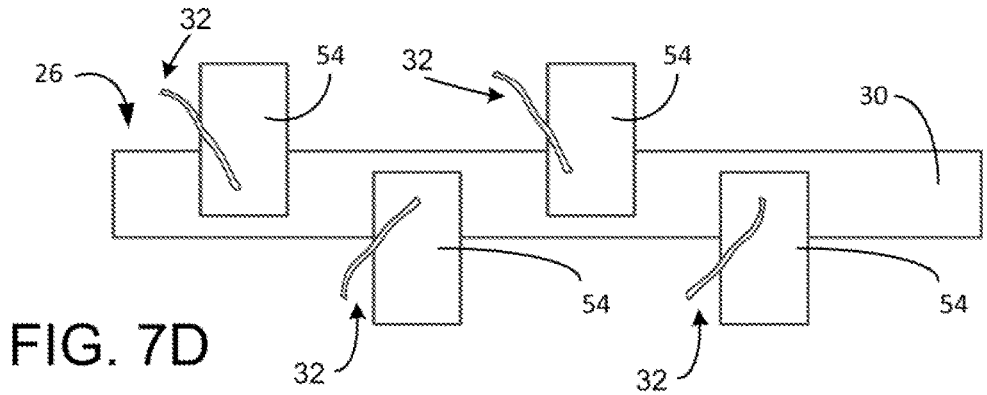
FIG. 7D shows a bottom view of a retainer in accordance with various embodiments.

FIG. 7B shows four clasping arms 54 extending from stem 30 and arranged symmetrically about the longitudinal axis of the retainer 26. On the other hand, FIG. 7C demonstrates in top view four clasping arms 54 extending from stem 30 and arranged asymmetrically about the longitudinal axis of the retainer 26. By providing the clasping arms 54, asymmetrically about the longitudinal axis of the retainer 26, there is an opportunity for the clasping arms 54 to interdigitate. FIG. 7D illustrates in bottom view the clasping arms 54 interdigitated. As with the other configurations of the clasping arms 54, the tag 32 can be attached to one or more clasping arms 54, including all of the clasping arms 54, to facilitate manipulation by the surgeon of the clasping arms 54, and therefore the electrode assembly 18.

FIGS. 8A-D show the retainer 26 in accordance with various embodiments. The retainer 26 is movable between a closed (resting) position (FIG. 8A) and an open (retracted) position 8B). In the closed position, the plurality of clasping arms 54 are configured to facilitate closure of the retainer 26 around the target tissue 20 to hold the electrode 24 in electrical communication, with the target tissue 20 and to hold the flexible sheath 28 around the target tissue 20. The electrode 24 is detachable from the at least one of the retainer 26 and the flexible sheath 28 when the retainer 26 is in the closed position around the target tissue 20. In the open position, the plurality of clasping arms 54 are configured to be held in an open position to facilitate initial placement of the retainer 26 around the target tissue 20 to hold the electrode 24 in electrical communication with the target tissue 20, or to facilitate removal of the retainer 26 from the target tissue 20. The plurality of clasping arms 54 may interdigitate in the closed position.

Figure 8A:
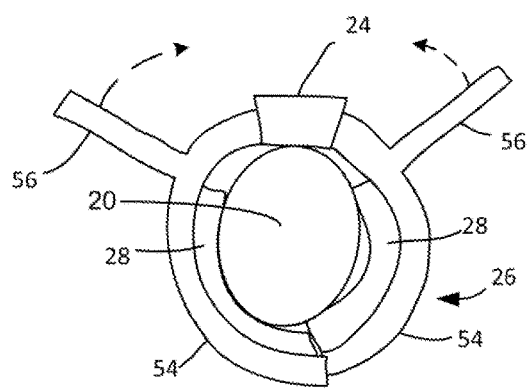
FIG. 8A illustrates a front elevational view of a closed position of a winglike flange on a retainer in accordance with various embodiments.
Figure 8C:
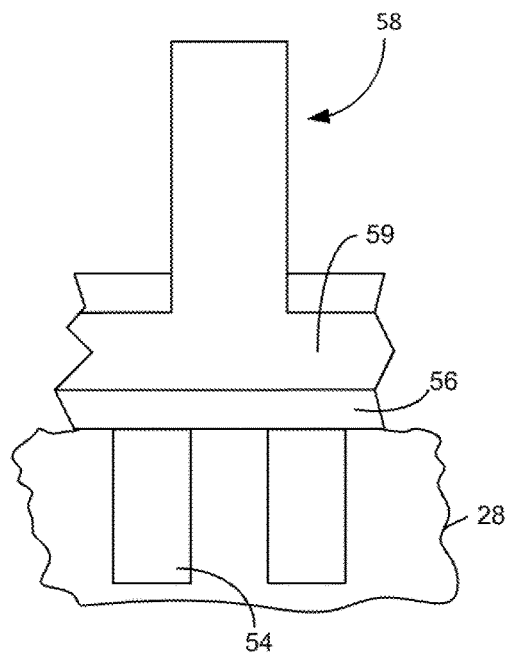
FIG. 8C illustrates a side view of a winglike flange on a retainer and forceps in accordance with various embodiments.
Figure 8B:
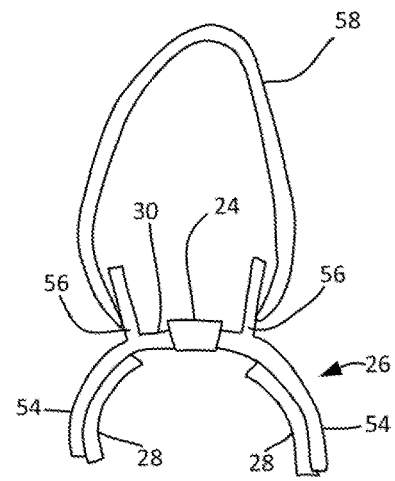
FIG. 8B illustrates a front elevational view of an open position of a winglike flange on a retainer in accordance with various embodiments.
Figure 8D:
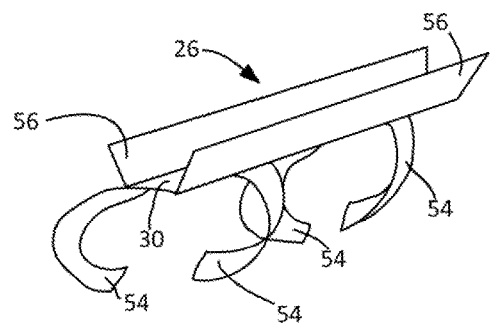
FIG. 8D illustrates a perspective view of a winglike flange on a retainer in accordance with various embodiments.
Figure 9A:
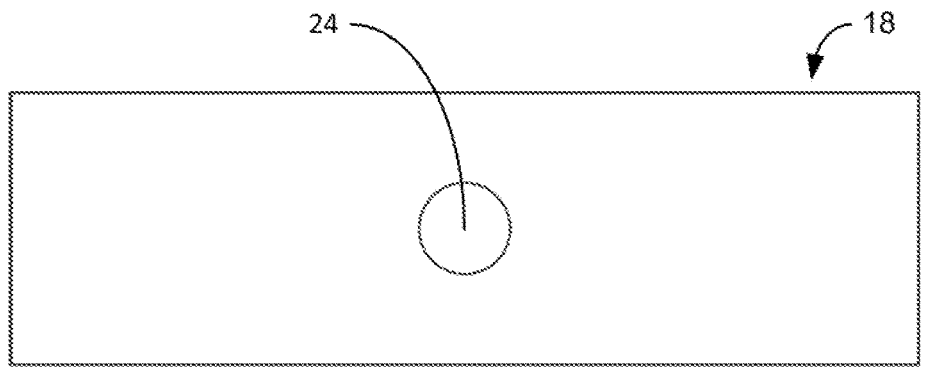
FIGS. 9A-C demonstrate electrode assemblies with different numbers of electrodes in accordance with various embodiments.
Figure 9B:
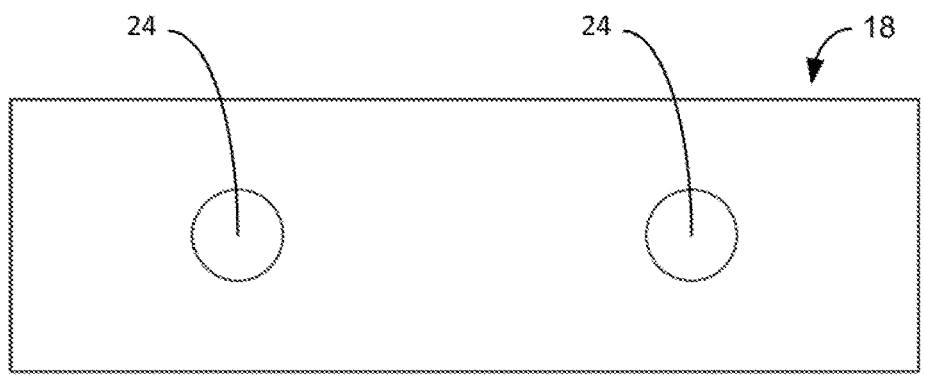
Figure 9C:
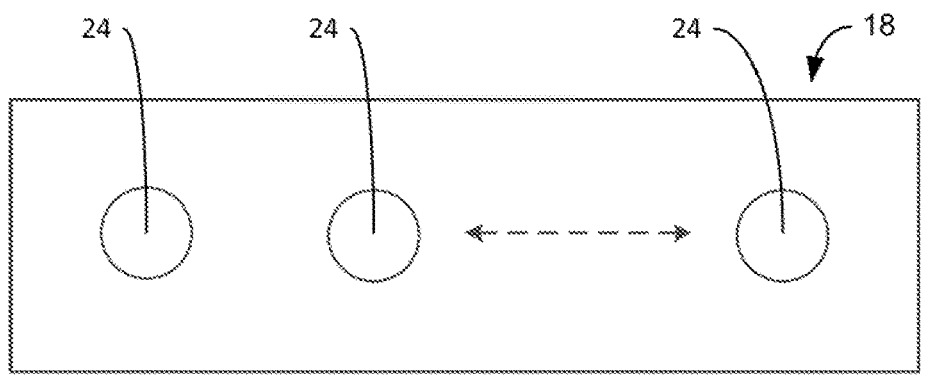
Figure 10A:
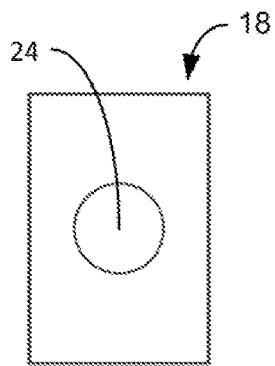
FIGS. 10A-C show leads with different numbers of electrode assemblies in accordance with various embodiments.
Figure 10B:
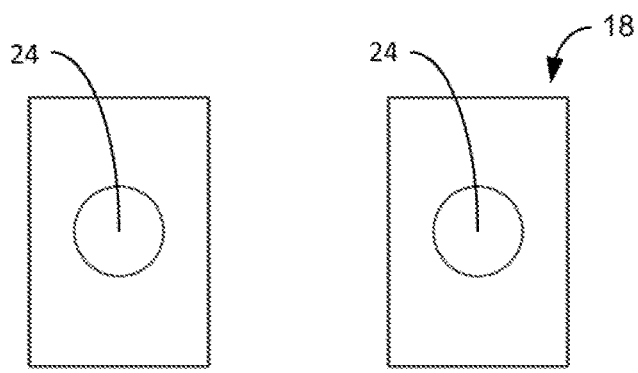
Figure 10C:
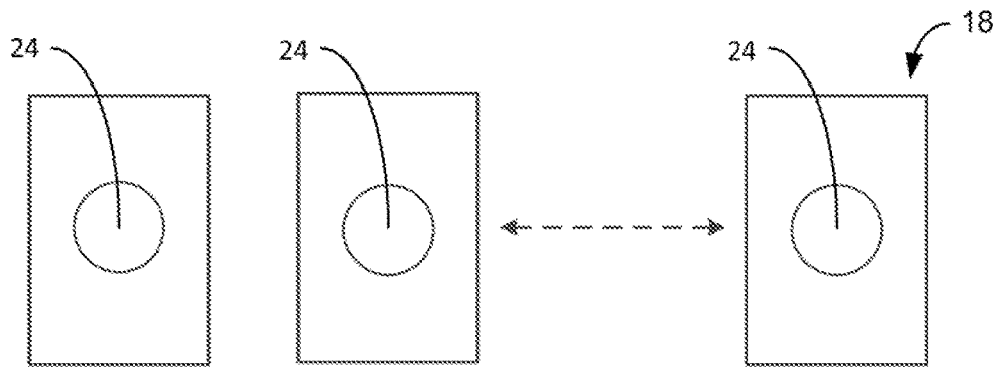

A variety of mechanisms can be used to implement movement of the retainer 26 between the closed position and the open position. In the embodiment shown in FIGS. 8A-D, the retainer 26 includes a pair of winglike (also known as butterfly) flanges 56 which extend from the stem 30 (FIG. 8D). The retainer 26 can be moved to the open position (FIG. 8B) by pinching the two winglike flanges 56 together for example by a forceps 58. In the open position, the clasping arms 54 of the retainer 26 are retracted for application of the retainer 26 around the target tissue 20 (FIG. 8B). Once the retainer 26 has been applied around the target tissue 20 and the clasping arms 54 have been put in a position surrounding the target tissue 20, the pinching action applied by the forceps 58 is removed, and the electrode 24 is held in electrical communication with the target tissue 20 by the retainer 26 (FIG. 8A).

The winglike flanges 56 of the retainer 26 may be retracted by any suitable mechanism or tool, including, but not limited to the forceps 58. As noted previously, when the winglike flanges 56 are retracted to place the retainer 26 in the open position, the retainer 26 can be placed around the target tissue 20 or removed from the target tissue 20. Forceps 58 are a hinged instrument that can be used for grasping and holding the retainer 26, and in particular the pair of winglike flanges 56. In one embodiment shown in FIG. 8C, the forceps 58 have a T-portion 59 that in use extends substantially parallel to a longitudinal axis of the winglike flanges 56, which will facilitate easy opening and closing of the winglike flanges 56 in one action by the surgeon.

FIGS. 9A-C and 10A-C demonstrates that the electrode 24 may be present in 1, 2, or N number in the electrode assembly 18 and the electrode 24 may be present as one electrode in 1, 2, or N number of electrode assemblies 18, respectively, in accordance with various embodiments. For example, the electrode assembly 18 may comprise 1, 2, 3, 4, 5, 6, 7, 8, 9, 10, 11, 12, 13, 14, 15 or more electrodes 24. Of course, any combination of electrodes and electrode assemblies is contemplated and possible.

Figure 11:
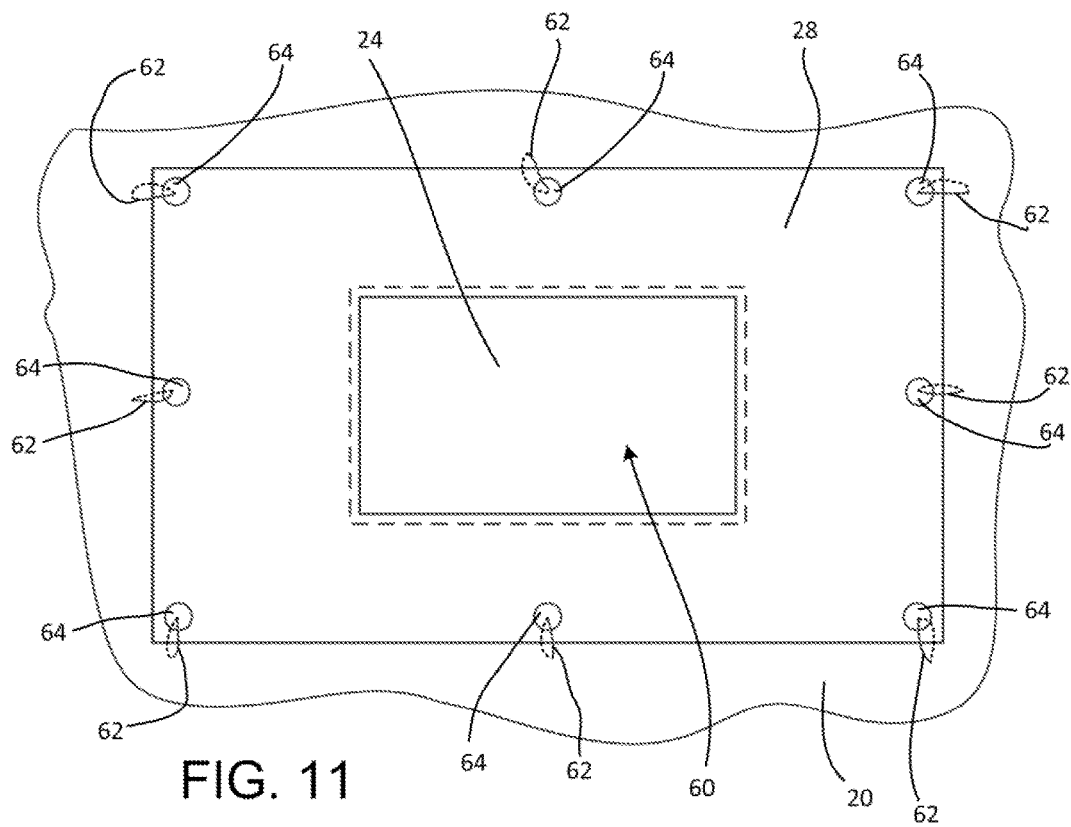
FIG. 11 is a top view of an electrode assembly in accordance with various embodiments.

FIG. 11 illustrates an alternate embodiment in which the flexible sheath 28 is coupled to the electrode 24 to retain the electrode 24 in electrical communication with the target tissue 20 wherein the flexible sheath 28 is directly attached to the target tissue 20. The flexible sheath 28 has an aperture 60 adapted to facilitate retention of the electrode 24 and to facilitate removal of the electrode 24 from electrical communication with the target tissue while the flexible sheath 28 remains adjacent the target tissue 20. The facilitation of retention of the electrode 24, and removal of the electrode 24, may be carried out in a variety of ways. By way of example, but not by way of limitation, a retention lip provided by the flexible sheath 28 and a retention edge provided by the electrode 24 have been discussed earlier.

In addition, FIG. 11 demonstrates an embodiment which utilizes an alternate retaining means for attaching the flexible sheath 28 and electrode 24 to the target tissue 20. For example, the retainer 26 may be a one or more sutures, designated by reference numeral 62 that attaches the flexible sheath 28 to the target tissue 20. The flexible sheath 28 provides a plurality of retainer apertures 64 around the perimeter of the flexible sheath 28 such that the surgeon can suture the flexible sheath 28 to the target tissue 20 by a series of single sutures 62 such as shown in FIG. 11. It will be understood by a person of ordinary skill in the art that alternately the sutures 62 can be a running suture, or some combination of single sutures and running sutures. Suture would not typically be used in delicate tissue such as nervous tissue, like a nerve. Rather, sutures 62 could be more typically used in non-delicate tissues, including, but not limited to, voluntary muscle, cardiac muscle, solid organs, and fascia.

Figure 12:
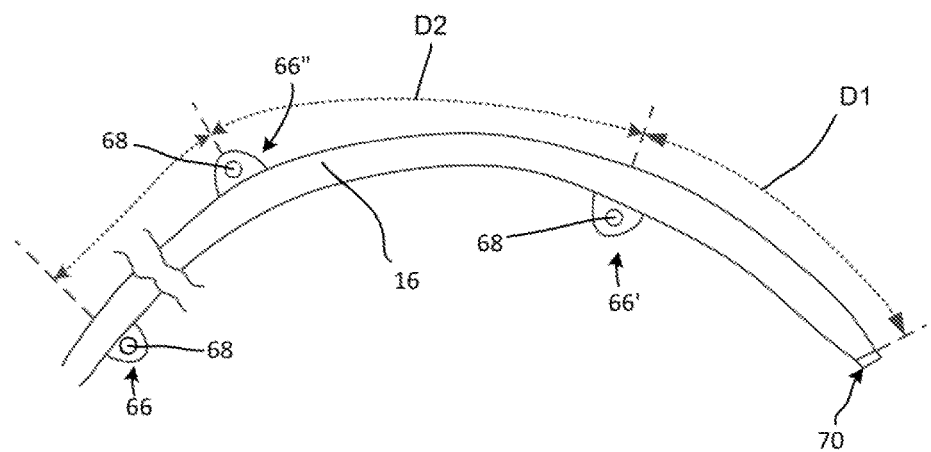
FIG. 12 shows a top view of the lead wire in accordance with various embodiments.

FIG. 12 demonstrates a series of separate lead wire anchors 66 on the lead wire 16 in accordance with various embodiments. After the surgeon has placed the electrode assembly 18 in the body, it is desirable that the lead wire 16 be "tacked down" in some way between the electrode assembly 18 and the IMD 14. By providing a series of lead wire anchors 66 at predetermined distances on the lead wire 16 with eyelets 68 that are premade, the surgeon will be able to suture the lead wire 16 in place with improved rapidity and consistency. The lead wire anchors 66 may be placed at substantially the same location along the lead wire 16 or distance from each other, including from a loop of the lead wire 16 that may be left in the body during the surgical procedure (see FIG. 1) that may relieve tension on the lead wire 16, in patients of various sizes, such as adults and children. For example, a distance D1 from an end 70 of the lead wire 16 that goes from the electrode 24 to a first lead wire anchor 66' may be about 2 to about 2.5 cm, and a distance D2 from the first lead wire anchor 66' to a second lead wire anchor 66" may be about 3 cm. The lead wire anchors 66 and eyelets 68 can be located at any orientation and distance along the lead wire 16, and such orientation and distance location can help in placement and mechanical stability of the lead wire 16 at different orientations in relation to the tissue to which the lead wire 16 is attached. The lead wire anchor 66 may be made of a plastic, or other biocompatible material, extension from the lead wire 16. Any number of lead wire anchors 66 may be used on the lead wire 16, however three may an optimal number.

Figure 13:
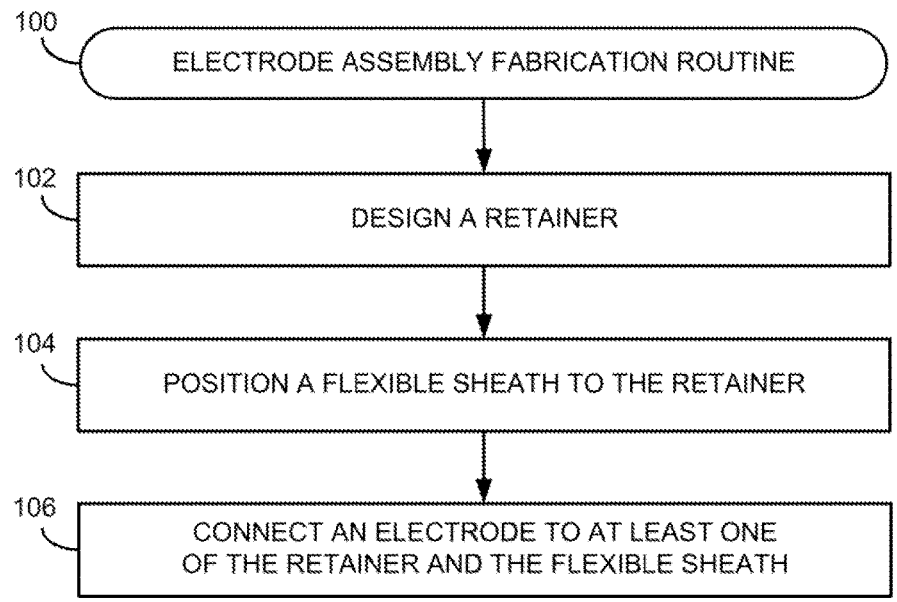
FIG. 13 shows a flowchart of fabricating an electrode assembly in accordance with various embodiments.

FIG. 13 illustrates an example electrode assembly fabrication routine 100 performed in accordance with various embodiments. While not required or limited to a particular method for constructing an electrode assembly, the routine 100 can begin in some embodiments by designing a retainer in step 102 that exhibits predetermined size and shape memory. As discussed above, design of a retainer can tune the material composition and thickness to produce a size and shape that facilitates retention of the retainer adjacent a target tissue. The retainer is designed to include a plurality of clasping arms and to be movable between an open position and a closed position.

With the retainer designed, step 104 includes positioning a flexible sheath below a lower surface of the retainer. The flexible sheath is at least partially surrounded by the clasping arms of the retainer. The retainer is able to hold the flexible sheath adjacent the target tissue when the retainer is in the closed position. Further, in some embodiments, the retainer is able to hold the flexible sheath around the target tissue when the retainer is in the closed position. In step 106, an electrode is connected to at least one of the retainer and the flexible sheath. The electrode is for conducting electrical signals to and from the target tissue. The retainer is able to hold the electrode in electrical communication with the target tissue when the retainer is disposed around the target tissue in the closed position. Through the various decisions and steps of routine 100, an electrode assembly can be fabricated and precisely tuned to provide predetermined operational characteristics. However, routine 100 is not limited to the steps shown in FIG. 13 as the various steps can be omitted, changed, and added.

Figure 14:
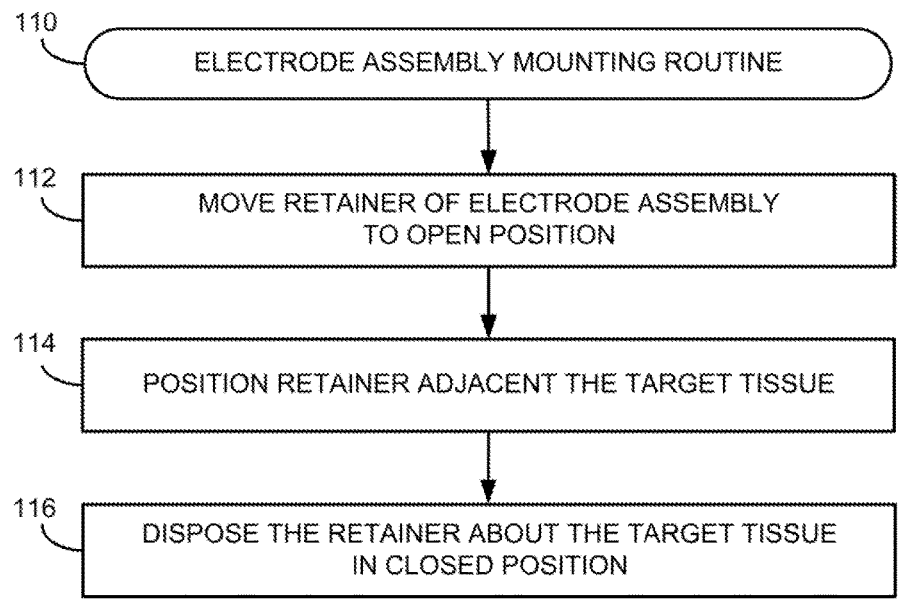
FIG. 14 provides a flowchart of mounting an electrode assembly in accordance with various embodiments.

FIG. 14 illustrates an example electrode assembly mounting on a target tissue routine 110 performed in accordance with various embodiments. While not required or limited to a particular method for mounting an electrode assembly, the routine 110 can begin in some embodiments by the surgeon exposing or freeing up a portion of a target tissue, such as a nerve. The exposure may be at least about 3 cm, although more or less freeing up of the target tissue may be performed in step 112, a retainer of the electrode assembly is moved to the open position. The retainer includes a plurality of clasping arms, and the retainer is movable between the open position and a closed position. In step 114, the retainer is positioned adjacent the target tissue. A flexible sheath is positioned below a lower surface of the retainer and at least partially surrounded by the clasping arms of the retainer. The retainer is able to hold the flexible sheath adjacent the target tissue when the retainer is in the closed position. In other embodiments, the retainer is able to hold the flexible sheath around the target tissue when the retainer is in the closed position. In step 116, the retainer is disposed around the target tissue in the closed position. The retainer is able to hold the electrode in electrical communication with the target tissue. The electrode is connected to at least one of the retainer and the flexible sheath. The electrode is for conducting, signals to and from the target tissue.

Through the various decisions and steps of routine 110, an electrode assembly can be mounted on a target tissue to hold an electrode in electrical communication with the target tissue, such that the electrode conducts signals to and from the target tissue. However, routine 110 is not limited, to the steps shown in FIG. 14 as the various steps can be omitted, changed, and added.

The present disclosure describes an implantable electrode assembly, such as a nerve cuff and electrode device which avoids the previous problems associated with placement and removal of prior electrode devices. The nerve cuff of the presently disclosed inventive concepts comprises one or more retainers which can be opened and closed in the manner of a hair clip. The electrode is attached to the retainer. The retainer is outside of and partially surrounds a flexible sheath which opens and closes as the retainer is opened and closed. The flexible sheath may be constructed of a elastomeric polymer material, such as but not limited to Silastic® silicone rubber. (Silastic is a registered trademark of Dow Corning Corporation, 2220 West Salzburg Rd., Midland, Mich., at the time this provisional application is filed.) The device is placed around a nerve with the sheath against the nerve and the retainer closed around the sheath and the electrode touching the nerve. The retainer is easier to apply than the currently used products thus eliminating much of the possibility of nerve damage when it is applied. If it is desired to remove the electrode from the nerve, e.g., when the nerve is infected, the retainer is detached from the sheath and the electrode or both the electrode and retainer are removed, leaving the flexible sheath in place on the nerve. This minimizes the damage to the nerve when the electrode is removed because the fibrotic tissue that is disturbed during removal is substantially not connected to the nerve. The disclosure also contemplates "eyelets" on the electrode lead for attaching the lead to tissue internally to keep the lead from moving.

It is to be understood that even though numerous characteristics and advantages of various embodiments of the present disclosure have been set forth in the foregoing description, together with details of the structure and function of various embodiments disclosed, this detailed description is illustrative only, and changes may be made in detail, especially in matters of structure and arrangements of parts within the principles of the present disclosure to the full extent indicated by the broad general meaning of the terms in which the appended claims are expressed.

What is claimed is:

1. An electrode apparatus comprising:
   a retainer comprising a stem and at least three clasping arms extending from the stem and movable between an open position and a closed position;
   a flexible sheath positioned below a lower surface of the retainer and at least partially surrounded by the at least three clasping arms of the retainer, the retainer is configured to hold the flexible sheath in contacting engagement around a target tissue when the retainer is in the closed position; and
   an electrode configured for conducting electrical signals to or from the target tissue, the electrode detachably connected and reattachable to the retainer, the retainer is configured to hold the electrode in electrical communication with the target tissue when the retainer is disposed around the target tissue in the closed position.

2. The electrode apparatus of claim 1, wherein the retainer is detachably connected to the flexible sheath.

3. The electrode apparatus of claim 2, wherein the retainer is detachable from the flexible sheath by severing one or more connectors between the flexible sheath and the retainer.

4. The electrode apparatus of claim 1, wherein the retainer is separable from the flexible sheath while the flexible sheath is configured to remain in engagement around the target tissue.

5. The electrode apparatus of claim 1, wherein the retainer is separable from the flexible sheath and movable to the open position to separate both the retainer and the electrode from the flexible sheath while the flexible sheath is configured to remain in engagement around the target tissue.

6. The electrode apparatus of claim 1, wherein the retainer comprises a winglike flange, wherein a first position of the winglike flange is configured to dispose the at least three clasping arms in the open position of the retainer for application of the retainer to the target tissue and a second position of the winglike flange is configured to dispose the at least three clasping arms in the closed position of the retainer for retention of the retainer around the target tissue.

7. An electrode apparatus comprising:
   a retainer comprising a stem and at least three clasping arms extending from the stem and movable to an open position and a closed position;
   a flexible sheath positioned below a lower surface of the retainer and at least partially surrounded by the at least three clasping arms of the retainer, the retainer is configured to hold the flexible sheath in contacting engagement around a target tissue when the retainer is in the closed position; and
   an electrode configured for conducting electrical signals to or from the target tissue, the electrode detachably connected to and reattachable to the retainer, the retainer is configured to hold the electrode in electrical communication with the target tissue when the retainer is disposed around the target tissue in the closed position;

an implantable medical device for transmitting or receiving the electrical signals; and a lead wire leading from the electrode to the implantable medical device for conducting the electrical signals between the electrode and the implantable medical device.

8. The electrode apparatus of claim 7, wherein at least one lead wire anchor is connected to the lead wire, and the at least one lead wire anchor is configured to enable a surgeon to suture the lead wire in place between the electrode and the implantable medical device.

9. The electrode apparatus of claim 8, wherein the at least one lead wire anchor provides an eyelet that is premade for the surgeon to suture the lead wire in the place.

10. The electrode apparatus of claim 8, wherein the at least one lead wire anchor is one of a series of separate lead wire anchors connected to the lead wire, and each of the series of separate lead wire anchors is premade in a manner to promote placement and mechanical stability of the lead wire that is sutured.

11. The electrode apparatus of claim 7, wherein the retainer is configured to separate from the flexible sheath and movable to the open position to separate both the retainer and the electrode from the flexible sheath while the flexible sheath remains around the target tissue.

* * * * *